United States Patent [19]

Livingston

[11] Patent Number: 4,568,741

[45] Date of Patent: Feb. 4, 1986

[54] SYNTHESIS OF 7-HALO-7-DEOXYLINCOMYCINS

[75] Inventor: Douglas A. Livingston, Kalamazoo, Mich.

[73] Assignee: The Upjohn Company, Kalamazoo, Mich.

[21] Appl. No.: 610,364

[22] Filed: May 15, 1984

[51] Int. Cl.$^4$ .............................................. C07H 5/10
[52] U.S. Cl. .................................. 536/16.5; 536/16.2
[58] Field of Search .............................. 536/16.5, 16.2

[56] References Cited

U.S. PATENT DOCUMENTS

| | | |
|---|---|---|
| 3,435,025 | 3/1969 | Birkenmeyer . |
| 3,475,407 | 10/1969 | Birkenmeyer ...................... 536/16.5 |
| 3,496,163 | 2/1970 | Birkenmeyer et al. . |
| 3,509,127 | 4/1970 | Kagan et al. . |
| 3,574,186 | 4/1971 | Birkenmeyer et al. . |
| 3,714,141 | 1/1973 | Shepard ............................ 536/16.5 |
| 4,324,888 | 4/1982 | Rathbone .......................... 536/16.5 |

OTHER PUBLICATIONS

Eilingsfeld et al., Angew. Chem., 72, 836-845, (1960).
Eilingsfeld et al., Chem. Ber., 96, 2671-2690, (1963).
Evans et al., JOC 33, 1074-1076, (1968).
Ferre et al., Tet. Lett., 2161-2164, (1969).
Kikugawa et al., Chem. Pharm. Bull. 19, 2629-2630, (1971).
Bosshard et al., Helv. Chim. Acta. 42, 1653-1658, (1959).
Hepburn et al., J. Chem. Soc., Perkin I, 754-756, (1976).
Hepburn et al., Chem. & Ind. 664-665, (1974).
Edwards et al., Tetrahedron Letters, 2369-2370, (1973).
Dobs et al., Tetrahedron Letters 165-168, (1969).

Primary Examiner—Brown Johnnie R.
Attorney, Agent, or Firm—Sidney B. Williams, Jr.

[57] ABSTRACT

An improved process for preparing 7-halo-7-deoxylincomycins and analogs thereof. The compounds prepared have anti-bacterial activity.

11 Claims, No Drawings

SYNTHESIS OF 7-HALO-7-DEOXYLINCOMYCINS

BACKGROUND OF THE INVENTION

1. Field of the Invention

The present invention is an improved process for preparing 7-halo-7-deoxylincomycins, including clindamycin, and pharmaceutically acceptable forms thereof from lincomycin and analogs thereof. Clindamycin is a well known antibiotic that has pharmacologically useful properties.

2. Prior Art

Processes for preparing 7-halo-7-deoxylincomycins are known. U.S. Pat. Nos. 3,435,025, 3,496,163 and 3,509,127 disclose a process in which the 7-hydroxyl group of lincomycin and analogous compounds are replaced with a halogen group by reacting said compounds with a Rydon reagent and heating the resulting product. The use of thionyl chloride to convert lincomycin and analogous compounds to 7-chloro-7-deoxy compounds is described in U.S. Pat. Nos. 3,496,163, 3,509,127 and 3,574,186. A process for preparing 7-halo-7-deoxylincomycin by the use of a sulfite-protected lincomycin and Rydon reagents is described in U.S. Pat. No. 3,714,141.

The use of a Vilsmeier reagent to substitute a halo atom for a hydroxyl group has been described. Eilingsfeld et al, Angew. Chem. 72, 836 (1960) and Eilingsfeld et al, Chem. Ber. 96 2671 (1963). Evans et al, JOC 33, 1074 (1968) discloses on page 1075 that while a Vilsmeier reagent prepared from methanesulfonyl chloride and dimethylformamide was successfully used to replace a primary hydroxyl group, it was not in attempts to replace a secondary hydroxyl group.

The structure of the adduct formed between dimethylformamide and thionyl chloride from which sulfur dioxide has not been removed has been investigated by Ferre et al, Tet. Lett. 2161 (1969) and the conditions for converting the dimethylformamide thionyl chloride adduct to the corresponding amide chloride has been described; Kikagawa et al, Chem. Pharm. Bull. 19, 2629 (1971). Bosshard et al, Helv. Chim. Acta. 42, 1653 (1959) discloses the use of dimethyl formamide as a catalyst in the conversion of carboxylic acids to acid chlorides.

Hepburn et al, J. Chem. Soc. Perkin I, 754 (1976) and Hepburn et al, Chem. & Ind. 664 (1974) describes the use of amide chlorides obtained from Vilsmeier reagents to replace hydroxyl groups by chlorine or bromine groups. However, the hydroxyl containing compounds were relatively simple alcohols and did not approach the complexity of the lincomycin molecule.

The use of a mixture of mesyl chloride and N,N-dimethylformamide to replace primary groups of hexopyranosides by chlorine is described by Edwards et al, Tetrahedron Letters, 2369 (1973).

The halogenation of nucleosides by amide chlorides is described by Dobs et al, Tetrahedron Letters, 165 (1969).

While the prior art describes the use of both Vilsmeier reagents and amide chlorides obtained therefrom in reactions similar to that of the process of this instant invention, the prior art is confusing at best. This is particularly true with respect to whether or not it is preferred to use the Vilsmeier reagent or to remove sulfur dioxide from it and use the resulting amide chloride.

Applicant has found that the use of the amide chloride rather than the Vilsmeier reagents to convert lincomycin type compounds to 7-halo-7-deoxylincomycin type compounds provides increased yields and products of improved quality.

SUMMARY OF INVENTION 7-halo-7-deoxy lincomycin and analogs thereof are prepared by (a) reacting lincomycin or an analog of lincomycin with an amide halide to form a lincomycin adduct, (b) heating the adduct formed in step (a) to form a 7-halo-7-deoxy adduct of lincomycin, (c) hydrolyzing the 7-halo-7-deoxy adduct formed in (b) and (c) isolating the 7-halo-7-deoxy compound. Advantages of using amide halides rather than Vilsmeier reagents include increased yields of the 7-halo-deoxylincomycins and a reduction in the amount of by-products. Another advantage of the process of this invention is that hydrated lincomycin can be used without detrimental effects on the yields or quality of the product.

An example of the 7-halo-7-deoxy compounds prepared and the lincomycin-type starting material are shown in Chart A. They are clindamycin (I) and lincomycin (II). The process is illustrated schematically in Chart B.

DETAILED DESCRIPTION OF INVENTION

In step (a) lincomycin or an analog thereof either in its free form or as an anhydrous or hydrated salt is reacted with an amide halide. Amide chlorides, especially those prepared from N-formyl piperidine and dimethylformamide are preferred. The reaction is conducted in the presence of a solvent at a temperature of about −10° to 40° C. for a reaction time of about several minutes to several hours. Preferred reaction temperatures and times are about 0° to 5° C. and 10 to 30 minutes, respectively. Solvents that can be used include chlorinated hydrocarbons such as methylene chloride, 1,2-dichloroethane; various chlorinated aromatics (i.e. chlorobenzene, dichlorobenzene, etc.); acetonitrile, toluene, xylenes, benzene, mixtures thereof and even an excess of the amide chloride or its parent amide can serve as the solvent. Preferred solvents include: a 1:1 solution of methylene chloride and toluene; dichloroethane or methylene chloride. About three to six equivalents of amide halide per equivalent of lincomycin is used. The preferred ratio is about four to five to one. Conventional means such as evaporation, crystallization and combinations thereof can be used to recover the lincomycin adduct.

In some cases an inhibitor, 3-t-butyl-4-hydroxy-5-methylphenylsulfide is added to the reaction mixture in an effort to eliminate color from the product and increase yield. This is now regarded to be of questionable advantage.

In step (b) the lincomycin adduct is heated to a temperature of about 50° to 75° C. for a period of time of about 2 to 40 hrs. to yield a 7-halo-7-deoxy adduct of lincomycin. The temperature of this step will depend upon the particular amide halide used. When the amide halide used is prepared by reacting N-formyl piperidine or dimethyl formamide and thionyl chloride the temperature used is about 55° to 65° C.

In step (c) the 7-halo-7-deoxy adduct is hydrolyzed by quenching it in a cold solution of base to yield a 7-halo-7-deoxylincomycin. Any aqueous base can be used. The amount of base used should be sufficient to prevent the reaction mixture from becoming strongly acidic. Sodium hydroxide and potassium hydroxide are particularly effective. The product can be recovered by recrystallization, evaporation, extraction, chromatography or combinations thereof.

Starting materials for the process are lincomycin or its analogs and an amide halide prepared by reacting a formamide with reagents such as a thionyl halide, phosgene, oxalyl chloride, phosphorus pentahalide, etc., as described by Eilingsfield et al, Angew. Chem., above.

Lincomycin is a known antibiotic and methods for preparing it and its analogs are well known in the art and illustrated in U.S. Pat. Nos. 3,086,912, and 3,155,580. In addition to those described in the patents cited above analogs of lincomycin are also exemplified in U.S. Pat. No. 3,380,992, and by protected lincomycin and analogs such as methylthiolincosaminide, lincomycin-3,4-acetonide, 3,4-(para-t-butylbenzylidene)-lincomycin, 3,4-cumylidene-lincomycin, and 3,4-benzylidene-lincomycin. As used herein lincomycin or lincomycin analogs means the free base or their salts. The salts may be anhydrous or hydrated.

Amide halides are known and may be prepared by methods well known in the art; "Iminium Salts in Organic Chemistry" Vol. 9, part 2 of Advances in Organic Chemistry, H. Bohme & H. G. Viehe, ed. Wiley (1979). The amide halides used in the process of this invention have the formula III shown in Chart A, wherein hal is bromine or chlorine atom; $R_1$ and $R_2$ are the same or different and are selected from the group consisting of aryl, alkyl containing one to eight carbon atoms, inclusive, or the alkyl groups when taken together with the nitrogen atom to which they are attached form (a) heterocyclic rings containing carbon and nitrogen of four to eight ring atoms and (b) morpholino. The term aryl means phenyl, substituted phenyl, naphthyl, substituted naphthyl and other aryl groups that do not interfere with or contain substituents that interfere with the reaction between the amide halide and lincomycin or its analogs. Heterocyclic rings include piperidino, N-substituted piperazino, and pyrrolidino, hexahydroazepino, and octahydroazocino. They can be prepared by reacting a source of halide with a formamide. Sources of halide include thionyl bromide, thionyl chloride, phosgene, oxalyl chloride, phosphorus pentachloride, phosphorus penta-bromide and carbonyl dibromide. In the case of thionyl chloride, the reaction is typically conducted in the presence of a solvent at a temperature of about 30° to 60° C. for a period of about 10 min. to 3 hrs. under vacuum. The preferred reaction temperature and times are about 40° to 50° C. and 10 minutes to one hr, depending on the vacuum applied. In the process of this invention it is necessary that the conditions used be sufficient to substantially remove the sulfur dioxide from the mixture. It is believed that the presence of residual sulfur dioxide is quite detrimental to the yield and purity of the product. This is assumed to occur because of the formation of a 3,4-sulfide ester, a species taken to be unstable under the reaction conditions, the structure of which could also detrimentally affect the stereoselectivity of the reaction.

The amide halide can be recovered from the reaction mixture by conventional methods. Thionyl chloride and N-formyl piperidine or dimethylformamide are the preferred reagents used in the preparation of clindamycin.

The following described examples of the process for preparing 7-halo-deoxylincomycin and intermediates useful therein are indicative of the scope of this invention and are not to be construed as limitative.

Preparation 1—N-(Chloromethylene)-piperidinium chloride

Under dry nitrogen a solution of N-formyl piperidine (170 gm, 1.50 mol) in anhydrous diethyl ether (1.5 L), stirring rapidly at 5° C., is treated with gaseous phosgene (142 gm, 1.44 mol) over the course of 1.5 hours. Ice bath cooling is applied to maintain a temperature of less than 12° C. The resulting while solid is filtered off under dry nitrogen, in vacuum, to give 94.4% (228 gm, 1.36 mol) of N-(chloromethylene)-piperidinium chloride.

Preparation 2—N-(Chloromethylene)-N-methylmethanaminium chloride

Utilizing a procedure similar to that of Preparation 1, but beginning with dimethyl formamide (170 gm, 2.33 mol) and phosgene (228 gm, 2.31 mol), yield (252 gm, 1.97 mol) of N-(chloro-methylene)-N-methylmethanaminium chloride is obtained.

Preparation 3—N-(Chloromethylene)-pyrrolidinium chloride

Utilizing a procedure similar to that used in Preparation 1, but beginning with N-formyl pyrrolidine (258 gm, 2.60 mol) and phosgene (235 gm, 2.47 mol), 96.0% (364 gm, 2.37 mol) of N-(chloromethylene)-pyrrolidinium chloride is obtained.

Preparation 4—N-(Chloromethylene)-morpholinium chloride

Utilizing a procedure similar that used in Preparation 1, but beginning with N-formylmorpholine (346 gm, 3.01 mol) and phosgene (301 gm, 3.05 mol), a 65% yield (333 gm, 1.96 mol) of N-(chloromethylene)-morpholinium chloride is obtained.

Preparation 5—N-(Chloromethylene)-morpholinium chloride

Under dry nitrogen, a solution of N-formyl morpholine (50.6 gm) 440 mmol) in anhydrous diethyl ether (300 ml), stirring rapidly in an ice bath is treated dropwise with a solution of oxalyl chloride (50.8 gm, 400 mmol) in hexane (30 ml). After warming to room temperature for 30 minutes, the solid product is filtered off under dry nitrogen and dried in vacuum to give 91.5% (62.2 gm, 366 mmol) of N-(chloromethylene)-morpholinium chloride.

Preparation 6—N-(Chloromethylene)-piperidinium chloride

Under dry nitrogen, N-formyl piperidine (124 gm, 1.10 mol), rapidly stirring at −4° C., is treated dropwise over the course of 30 minutes with thionyl chloride (144 gm, 1.21 mol), the temperature being maintained below 0° C. with ice-methanol cooling. The resulting solution is warmed slowly to 56° C. over 80 minutes with the application of vacuum (at about 30 mm). A mixture of methylene chloride 10 ml and toluene (40 ml) is added, and the resulting slurry is concentrated to dryness (37° C., about 30 mm vacuum). This stripping procedure is repeated, and final concentration is accomplished by the application of higher (about 5 mm) vacuum (30°-42° C., 30 min), to yield solid N-(chloromethylene)-morpholinium chloride.

Preparation 7—N-(Chloromethylene)-N-methylmethaninium chloride

In a manner similar to that used in Preparation 6, dimethyl formamide (32.5 gm, 445 mmol) and thionyl chloride (58.2 gm, 490 mmol) are used to prepare N-(chloromethylene)-N-methylmethanaminium chloride.

EXAMPLE 1

Clindamycin hydrochloride hydrate (a) Adduct of lincomycin hydrochloride

Under dry nitrogen a slurry of N-(chloromethylene)-piperidinium chloride (36.2 gm, 215 mmol) in dichloroethane (100 ml), while being stirred rapidly and cooled in an ice bath is treated portionwise (15 min) with lincomycin hydrochloride hydrate (18.1 gm, 39.2 mmol), and then with an inhibitor, 3-4-butyl-4-hydroxy-5-methylphenylsulfide (0.17 gm), to yield a solution of an adduct of lincomycin hydrochloride.

(b) Adduct of clindamycin

The resulting mixture obtained in 1(a) is warmed to room temperature for 4 hours, then the temperature is ramped to to 60° C. over the course of 10 hours. After 4 hours at 60° C., then four hours at 65° C., a mixture containing an adduct of clindamycin is obtained.

(c) Clindamycin hydrochloride hydrate

The mixture of the adduct obtained in 1(b) is cooled to 0° C. then poured rapidly into sodium hydroxide (17.2 gm, 430 mmol) in water and ice (200 gm), with rapid stirring. The pH is reduced (with hydrochloric acid) to 10.5, and the mixture is stirred at room temperature two hours, then at pH=7 overnight. With ice-bath cooling, hydrochloric acid is added to adjust the pH to 1.5. This is then extracted with five (50 ml) portions of methylene chloride, each organic phase being washed in turn with three (75 ml) portions of dilute hydrochloric acid at pH=1.5. The aqueous phases are combined, adjusted (with aqueous sodium hydroxide) to pH=10.5, and extracted with five (50 ml) portions of methylene chloride. Each organic extract is washed sequentially through two (75 ml) portions of 0.5 molar phosphate buffer at pH 6.2. The combined organic phases are dried over sodium sulfate, filtered, and concentrated to an oil. The oil is taken up in ethyl acetate (200 ml). The solvent is stripped under vacuum, and the stripping procedure is repeated. The resulting oil is taken up in an additional portion of ethyl acetate and subjected to decolorization with 5% activated carbon (0.9 gm Darco G-60, 30 min), filtered (through Celite 454), and reconcentrated to an oil. This is dissolved in ethyl acetate (81 ml) and ethanol (absolute 23 ml), and concentrated hydrochloric acid is added (with rapid stirring) to a final pH of 0.5. The resulting slurry is stirred for one hour at room temperature, then for 30 minutes at 0° C. The solids are filtered off, washed with ethyl acetate (10 ml), and dried overnight at 80° C. under vacuum to give 93.5% (18.6 gm, 36.6 mmol) of clindamycin hydrochloride ethanol solvate. A portion of this (17.7 gm, 34.9 mmol) is dissolved in water (30 ml), and stripped to a heavy syrup (30 ml). Boiling acetone (415 ml) is added with swirling, the solution is seeded, and stirred while allowing it to cool slowly to room temperature (4 hr) during the crystallization. After stirring 30 minutes in an ice bath, the white, crystalline product is filtered off and dried in a stream of air to give 96.9% (16.2 gm, 33.8 mmol), giving 90.6% overall, of clindamycin hydrochloride hydrate.

EXAMPLE 2

Clindamycin hydrochloride hydrate (a) Adduct of lincomycin hydrochloride hydrate Under dry nitrogen, a slurry of N-(chloromethylene)-N-methylmethaninium chloride prepared in Preparation 2 (22.9 gm, 179 mmol) in dichloroethane (56 ml), stirred rapidly and cooled in an ice bath is treated portionwise (15 min) with lincomycin hydrochloride hydrate (15.0 gm, 32.5 mmol) and then with 3-t-butyl-4-hydroxy-5-methylphenyl sulfide (0.15 gm) to yield an adduct of lincomycin.

(b) Clindamycin adduct

The adduct obtained in 2(a) is warmed to room temperature for two hours and then ramped to 60° C. over the course of ten hours. After six hours at 60° C. then five hours at 68° C., a solution containing an adduct of clindamycin is obtained.

(c) Clindamycin hydrochloride hydrate

The solution prepared in (b) is cooled to 0° C., then quenched into sodium hydroxide (10.7 gm, 268 mmol) in water and ice (100 gm). The temperature is kept below 21° C. by application of an ice-acetone bath, and the pH is maintained above 6 during the quench by the addition of additional aqueous sodium hydroxide. The mixture is stirred at pH=10.5 at room temperature four two hours, then at pH=7 overnight.

Work-up and crystallization exactly analogous to that of Example 1, above, gives 90.4% (14.9 gm, 29.4 mmol) of clindamycin hydrochloride ethanol solvate. A portion (14.3 gm, 28.1 mmol) is taken (as above) to clindamycin hydrochloride hydrate in 94.8% yield (12.8 gm, 26.7 mmol), giving 85.7% overall yield.

EXAMPLE 3

Clindamycin hydrochloride hydrate (a) Adduct of lincomycin

Under dry nitrogen, a slurry of N-(chloromethylene)-pyrrolidinium chloride (33.0 gm, 215 mmol) in dichloroethane (80 ml), stirring rapidly and cooled in an ice bath is treated portionwise (20 min) with lincomycin hydrochloride hydrate (18.0 gm, 39.0 mmol) and then with an inhibitor, 3-t-butyl-4-hydroxy-5-methylphenyl sulfide (0.18 gm), to yield a solution of lincomycin adduct.

(b) Clindamycin adduct

The solution of lincomycin adduct obtained in 3(a) is warmed to room temperature for an hour, then the temperature is ramped to 60° over the course of 16 hours. After 45 hours at 60° to 65° C., there is obtained a solution of clindamycin adduct.

(c) clindamycin hydrochloride hydrate

The solution of adduct obtained in 3(b) is cooled to 0° C., then poured rapidly into sodium hydroxide (15.5 gm, 388 mmol) in water and ice (200 gm), with rapid stirring. Additional aqueous sodium hydroxide is added to maintain a pH greater than 8. The pH is adjusted to 10.0, the mixture is stirred at room temperature for 3 hours, then the pH is reduced 7.0.

Work-up and crystallization, as above, gives 89.8% (17.8 gm, 35.0 mmol) of clindamycin hydrochloride ethanol solvate. A portion of the solvate (16.8 gm, 32.4 mmol) is taken as in Example 2 to clindamycin hydrochloride hydrate, yielding 94.3% (14.6 gm, 30.5 mmol), giving 84.7% overall yield.

EXAMPLE 4

Clindamycin hydrochloride hydrate (a) Adduct of lincomycin hydrochloride

Under dry nitrogen, a slurry of the N-(chloromethylene)-morpholinium chloride (37.1 gm, 218 mmol, obtained in Preparation 4) in dichloroethane (90 ml), is treated portionwise with lincomycin hydrochloride hydrate (18.3 gm, 39.6 mmol) and then with 3-t-butyl-4-hydroxy-5-methylphenyl sulfide (0.19 gm). Residual solids are washed with dichloroethane (10 ml) and then with methylene chloride (10 ml), to provide a mixture of lincomycin hydrochloride adduct.

(b) Adduct of clindamycin

The mixture is warmed to room temperature for 3 hours, then the temperature is ramped to 45° C. over the course of 2 hours. After 16 hours at 45° C., then 6 hours at 60° C., the solution is cooled to 0° C.

(c) Clindamycin hydrochloride hydrate

The solution obtained in 4(b) is then poured rapidly into sodium hydroxide (17.5 gm, 438 mmol) in water and ice (200 gm), with rapid stirring. The pH is reduced (with hydrochloric acid) to 10.5, the mixture stirred at room temperature for 30 minutes, then the pH is reduced further to 1.5.

Work-up and crystallization similar to that of Preparation 2, above, gives 78.7% (15.8 gm, 31.2 mmol) of clindamycin hydrochloride ethanol solvate. A portion (14.4 gm, 28.4 mmol) is taken (as in Example 1) to clindamycin hydrochloride hydrate in 93.0% yield (12.7 gm, 26.4 mmol), giving 73.1% overall yield.

EXAMPLE 5

Clindamycin hydrochloride hydrate (a) Adduct of lincomycin hydrochloride

Under dry nitrogen, a rapidly stirring slurry of anhydrous lincomycin hydrochloride (10.7 gm, 24.2 mmol) in acetonitrile (15 ml) is treated over the course of an hour with a slurry of N-(chloromethylene)-morpholinium chloride obtained in Preparation 5 (18.3 gm, 109 mmol) in acetonitrile (40 ml) to give lincomycin hydrochloride adduct.

(b) Clindamycin adduct

The adduct obtained in 5(a) is heated at about 52° C. for one hour and then refluxed for 30 minutes to yield the adduct of clindamycin.

(c) Clindamycin hydrochloride hydrate

The solution of the adduct obtained in 5(b) is cooled to 0° and quenched with anhydrous methanol (30 ml). After stirring at room temperature overnight, then concentrating under vacuum, the residue is taken up in ethyl acetate and washed with cold, aqueous (10%) sodium hydroxide. The aqueous phase is reextracted twice with ethyl acetate, the combined organic phases are dried (magnesium sulfate), filtered, subjected to decolorization with activated carbon (Darco G-60, 0.5 gm, 1 hr), filtered (through Celite 454), and concentrated under vacuum (to 40 gm). Ethyl acetate is added (to a total weight of 63 gm), then anhydrous ethanol (13 ml), and concentrated hydrochloric acid is added dropwise, with rapid stirring to a final pH of 1. After stirring at room temperature one hour, the resulting solid is filtered off and dried under vacuum to constant weight, giving 78.6% (9.66 gm, 19.0 mmol) of clindamycin hydrochloride ethanol solvate. A portion (8.57 gm, 16.9 mmol) is taken (as in Example 1, above), to clindamycin hydrochloride hydrate in 89.3% yield (7.24 gm, 15.1 mmol), giving 70.2% overall yield.

EXAMPLE 6

Clindamycin hydrochloride hydrate (a) Lincomycin hydrochloride adduct

Under dry nitrogen, a mixture of N-(chloromethylene)-piperidinium chloride prepared in Preparation 6 (300 ml), while being stirred rapidly at −4° C., is treated with lincomycin hydrochloride hydrate (80.0 gm, 174 mmol) in portions over the course of 25 minutes, and then 3-t-butyl-4-hydroxy-5-methylphenyl sulfide (0.80 gm). Residual solids are rinsed in with 50 ml of methylene chloride to provide a mixture of lincomycin hydrochloride adduct.

(b) Clindamycin adduct

The mixture of lincomycin hydrochloride adduct obtained in 6(a) is heated slowly (30 min) to reflux. Solvent is distilled off, and toluene (175 ml) is added at an equivalent rate, over the course of 1.5 hours, to a final temperature of 52° C. Refluxing 16 hours brought the temperature to 57° C. to obtain a mixture of the adduct of clindamycin.

(c) Clindamycin hydrochloride hydrate

The mixture of the adduct obtained in 6(b) is cooled to 0° C. and quenched into sodium hydroxide (47.0 gm, 1.18 mmol) in cold water (500 ml). Work-up and crystallization in a manner similar to that used in Example 1, provides 97.2% (85.6 gm, 169 mmol) of clindamycin hydrochloride ethanol solvate. A portion of this (85.1 gm, 168 mmol) is converted into clindamycin hydrochloride hydrate (as in Example 2) in 93.0% yield (74.8 gm, 156 mmol), giving 90.4% overall.

EXAMPLE 7

Clindamycin hydrochloride hydrate

In a manner similar to that used in Example 6, N-(chloromethylene)-methylmethanaminium is used to convert lincomycin hydrochloride hydrate (32.8 gm, 71.2 mmol) into clindamycin hydrochloride ethanol solvate in 88.9% yield (32.1 gm, 63.3 mmol). A portion of this (30.5 gm, 60.6 mmol), is converted into clindamycin hydrochloride hydrate (as above) in 90.1% yield (25.9 gm, 54.1 mmol) giving 80.1% overall yield.

EXAMPLE 8

Clindamycin hydrochloride hydrate

In a procedure similar to that used in Example 6, but substituting substantially anhydrous lincomycin hydrochloride (containing 1.3% water by Karl Fischer titration) for lincomycin hydrochloride hydrate there is obtained clindamycin hydrochloride hydrate in 86.0% overall yield.

EXAMPLE 9

Utilizing a procedure similar to that used in Examples 1 through 9 but substituting the following for lincomycin:
methylthiolincosaminide,
lincomycin-3,4-acetonide,
3,4-cumylidene lincomycin,
3,4-(para-t-butylbenzylidene)lincomycin,
3,4-benzylidene lincomycin,
there is obtained
7-chloromethylthiolincosaminide,
clindamycin-3,4-acetonide, 3,4-(para-t-butylbenzylidene)clindamycin, 3,4-cumylidene clindamycin and 3,4-benzylidene clindamycin, respectively.

CHART A

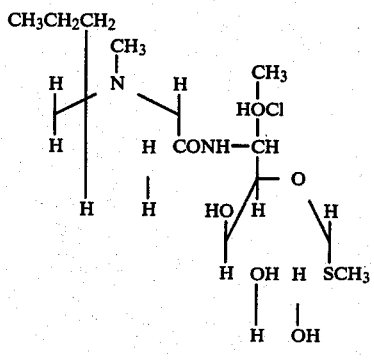

I

Clindamycin (7-halo-7-deoxylincomycin)

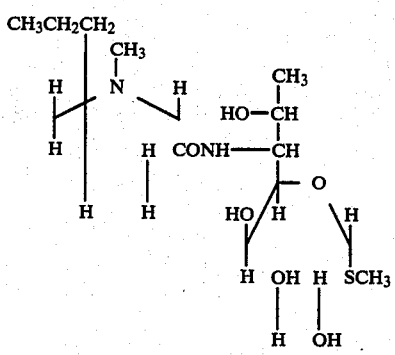

II

Lincomycin

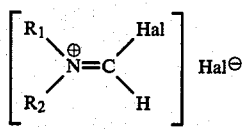

III

Amide Halide

CHART B

Lincomycin

↓ Amide chloride

Adduct of Lincomycin

↓ Heat

7-Halo-7-deoxy Adduct of Lincomycin

↓ hydrolysis

7-Halo-7-deoxy-lincomycin

I claim:
1. A process for preparing a compound selected from the group consisting of 7-halo-7-deoxylincomycin and analogs thereof which comprises
(a) reacting a compound selected from the group consisting of lincomycin and analogs thereof with an amide halide having the formula

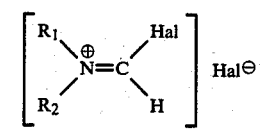
III wherein halogen is a bromine or chlorine atom, $R_1$ and $R_2$ are the same or different and are selected from the group consisting of aryl, alkyl containing one to eight carbon atoms, inclusive, or when taken together with the nitrogen atom to which they are attached form a heterocyclic ring selected from the group consisting of (a) a heterocyclic ring containing carbon and nitrogen of four to eight ring atoms and (b) morpholino;
(b) heating the adduct formed in step (a) to form a 7-halo-7-deoxy adduct; and
(c) hydrolyzing the 7-halo-7-deoxy adduct formed in step (b) with an aqueous base; and
(d) isolating the 7-halo-7-deoxylincomycin compound.
2. A process according to claim 1 wherein the amide halide is an amide chloride.
3. A process according to claim 2 wherein the amide chloride is selected from the group consisting of N-(chloromethylene)-N-methylmethanaminium chloride, N-(chloromethylene)-piperidinium chloride, N-(chloromethylene)-morpholinium chloride and N-(chloromethylene)-pyrrolidinium chloride.
4. A process according to claim 2 wherein the compound reacted in (a) is lincomycin so that the compound prepared is clindamycin.
5. A process according to claim 3 wherein the amide chloride is N-(chloromethylene)-N-methylmethanaminium chloride and the compound reacted in step (a) is hydrated lincomycin hydrochloride.
6. A process according to claim 3 wherein the amide chloride is N-(chloromethylene)-piperidinium chloride and the compound reacted in step (a) is hydrated lincomycin hydrochloride.

7. A process according to claim 5 or 6 wherein the compound reacted in step (a) is lincomycin hydrochloride hydrate and the compound prepared is clindamycin hydrochloride hydrate.

8. A process for preparing a lincomycin adduct which comprises reacting a compound selected from the group consisting of lincomycin and analogs thereof with an amide halide having the formula

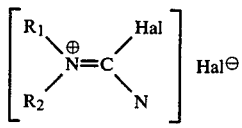 III wherein halogen a bromine or chlorine atom, $R_1$ and $R_2$ are the same or different and are selected from the group consisting of aryl, alkyl containing one to eight carbon atoms, inclusive, or when taken together with the nitrogen atom to which they are attached from a heterocyclic ring selected from the group consisting of (a) a heterocyclic ring containing carbon and nitrogen of four to eight ring atoms and (b) morpholino.

9. A process according to claim 8 wherein the amide halide is an amide chloride.

10. A process according to claim 9 wherein the amide chloride is selected from the group consisting of N-(chloromethylene)-N-methylmethanaminium chloride, N-(chloromethylene)-piperidinium chloride, N-(chloromethylene)-morpholinium chloride and N-(chloromethylene)-pyrrolidinium chloride.

11. A process according to claim 9 wherein the compound reacted in (a) is lincomycin so that the compound prepared is clindamycin.

* * * * *